(12) United States Patent
Mogford et al.

(10) Patent No.: US 10,926,136 B1
(45) Date of Patent: Feb. 23, 2021

(54) HEALTH MONITORING WITH 3D PRINTED SENSORS

(71) Applicant: Sciperio, Inc, Orlando, FL (US)

(72) Inventors: Jonathan Mogford, College Station, TX (US); Kenneth H. Church, Orlando, FL (US)

(73) Assignee: SCIPERIO, INC, Orlando, FL (US)

( * ) Notice: Subject to any disclaimer, the term of this patent is extended or adjusted under 35 U.S.C. 154(b) by 551 days.

(21) Appl. No.: 15/663,426

(22) Filed: Jul. 28, 2017

Related U.S. Application Data

(60) Provisional application No. 62/369,102, filed on Jul. 30, 2016.

(51) Int. Cl.
| | | |
|---|---|---|
| A63B 24/00 | (2006.01) | |
| A61B 5/11 | (2006.01) | |
| A63F 13/211 | (2014.01) | |
| A61M 35/00 | (2006.01) | |
| A61F 13/00 | (2006.01) | |
| A63F 13/218 | (2014.01) | |
| G09B 5/02 | (2006.01) | |
| A63B 71/06 | (2006.01) | |
| G09B 19/00 | (2006.01) | |
| A63B 23/03 | (2006.01) | |

(52) U.S. Cl.
CPC ............ *A63B 24/0075* (2013.01); *A61B 5/11* (2013.01); *A61F 13/00063* (2013.01); *A61M 35/00* (2013.01); *A63B 23/032* (2013.01); *A63B 71/0622* (2013.01); *A63F 13/211* (2014.09); *A63F 13/218* (2014.09); *G09B 5/02* (2013.01); *G09B 19/003* (2013.01); *A63B 2024/0096* (2013.01); *A63B 2071/0655* (2013.01); *A63B 2220/56* (2013.01); *A63B 2225/54* (2013.01)

(58) Field of Classification Search
CPC .............................. A61B 5/682; A63B 71/085
See application file for complete search history.

(56) References Cited

U.S. PATENT DOCUMENTS

| | | | |
|---|---|---|---|
| 10,201,399 B2 * | 2/2019 | Morgan | A63B 71/085 |
| 2005/0284489 A1 * | 12/2005 | Ambis, Jr. | A63B 71/085 |
| | | | 128/859 |
| 2012/0259648 A1 | 10/2012 | Mallon et al. | |
| 2012/0259649 A1 | 10/2012 | Mallon et al. | |
| 2012/0259650 A1 | 10/2012 | Mallon et al. | |
| 2012/0259651 A1 | 10/2012 | Mallon et al. | |
| 2012/0259652 A1 | 10/2012 | Mallon et al. | |
| 2013/0123667 A1 | 5/2013 | Komatireddy et al. | |
| 2013/0178960 A1 | 7/2013 | Sheehan et al. | |
| 2013/0217977 A9 | 8/2013 | Cooner | |
| 2014/0081661 A1 | 3/2014 | Fu et al. | |
| 2014/0322686 A1 | 10/2014 | Kang | |
| 2016/0367188 A1 * | 12/2016 | Malik | A61J 17/003 |
| 2017/0007363 A1 * | 1/2017 | Boronkay | G05B 19/042 |

* cited by examiner

*Primary Examiner* — Christine H Matthews
(74) *Attorney, Agent, or Firm* — Goodhue, Coleman & Owens, P.C.

(57) ABSTRACT

A personalized device for therapeutic training includes a therapeutic device body, electronic circuitry integrated into the therapeutic device body wherein the electronic circuitry comprises at least one sensor. The therapeutic device body is personalized for use by a patient through sizing and shaping the therapeutic device based on measurements of the patient and 3D printing at least a portion of the therapeutic device body and at least a portion of the electronic circuitry to make the personalized device both electrically and mechanically functional.

20 Claims, 6 Drawing Sheets

HEALTH MONITORING WITH 3D PRINTED SENSORS

RELATED APPLICATIONS

This application claims priority to U.S. Provisional Patent Application No. 62/369,102, filed Jul. 30, 2016, and entitled "Health Monitoring With 3D Printed Sensors", hereby incorporated by reference in its entirety.

FIELD OF THE INVENTION

The present invention relates generally to a personalized sensor and motion system to enable personalized health monitoring, physical rehabilitation and training.

BACKGROUND OF THE INVENTION

Each year, 50 percent of Americans over the age of 18 develop a musculoskeletal injury that lasts longer than 3 months. In 2007, (only) an estimated 9 million adults utilized outpatient physical therapy services. The average outpatient course of care is only between 7-10 visits and reimbursement rates and visits approved for physical therapy services are largely stagnant or decreasing. Even with decreasing coverage, only 30% of patients that utilize outpatient physical therapy services attend all of the visits that their insurance company authorizes per course of care. Moreover, only 30 percent of physical therapy patients are fully adherent with their plan of care. Thus, there are problems with those in need of physical therapy, occupational therapy or other forms of therapy receiving the needed therapy for a variety of reasons.

One specific example relates to oro-motor training. Current oro-motor training is done with a mouth piece or simple silicon rubber chew and instruction from a therapist. The patient is presented with verbal and/or visual direction by the therapist, which by nature is open-ended guidance. In other words, there is no objective or measurable mechanism for the patient or therapist to compare the patient's performance to the therapist's direction. This lack of closed-loop information flow may discourage the patient from putting forth their best efforts during the therapy session or returning for additional therapy sessions, despite the positive impact that therapy would provide on their condition.

In addition, other forms of current physical therapy may be performed with therapists providing verbal/visual guidance, physically stretching or moving a body part or manipulating a specific joint and then teaching a patient the motion. Patients will provide feedback to the therapists with verbal communication and adjustments are made.

Despite the benefits of therapy numerous problems remain. One of the problems is that the amount of therapy that a patient receives is limited by time constraints such as may be imposed by therapist availability, medical insurance coverage limitations, or other constraints. Thus, progress of a patient may be limited with respect to what is possible. Although a therapist or other health care provider may prescribe a particular regiment to patients, patients may not always follow the regiment and thus patent compliance issues remain.

What is needed are improved methods and systems for personalized health monitoring and training.

SUMMARY OF THE INVENTION

Therefore it is a primary object, feature, or advantage to personalize a sensor and motion system for observation and training each individual. The personalized system may use specific sensing in strategic locations on the body which extracts relevant biophysical information on each individual. The personalized system may also impart specific motion to those strategic locations on the body. The system may connect to a device that can store the biophysical data that can be used by an individual for health self-monitoring (for personalized training, physical rehabilitation, injury avoidance due to improper or excessive motion/exertion), can be used by a health care provider (for objective measurement of patient performance, to increase/improve patient engagement/compliance, to support personalized tele-rehabilitative sessions, to build/contribute to an evidence-focused population/procedure database, to support an evidence-based reimbursement system), can be used by health care payers via an evidence-based reimbursement system (e.g. pay for efficacy), or otherwise. Personalizing the training may happen through data mining, personalized sensing devices such as a mouth piece, a brace or bandage/applique for any joint (including the neck, knee, wrist or ankle) and the necessary corrective motion provided via tactile, visual or other types of feedback established by the health care provider (e.g. the system may impose limits to force, rang-of-motion or type/rate of motion) based on the patient's status or even through data comparison to like populations. There is limited-to-nonexistent data on each person that needs training but the data base will continue to grow and data mining will be important to locate and compare to each individual being trained. For example, the personalized mouth piece is a personal fit with wireless sensors to measure and transmit all aspects of motion (force, rate, direction), pressure and location of the pressure. Software to compare the data mined from similar cases to those collected from the wireless sensor mouth piece will provide information on additional therapy. The wireless sensor may also add to the growing data base providing more information. Similarly, other types of personal health devices may be fitted the human body appropriate and provide for collection of any anatomic biophysical data.

Another important attribute of this approach is the 3D-printed electrically functional device (i.e., mouth piece, skin applique or brace). Using a computed tomography (CT) scan or other scanning technique to obtain the shape of the mouth, the knee or any portion of the body, the device can be personalized and made to fit each individual. Additionally, the made-to-fit device can be printed with electronic function. Electronic function includes a variety of sensors (such as, but not limited to force, rate, range-of-motion) and a wireless transmitter to allow the individual to chew the mouth piece without interference or to move any bodily joint without restriction.

According to one aspect, oro-motor training may be improved. As previously explained, current oro-motor training is done with a mouth piece and instruction from a therapist. The patient must follow the instructions of the therapist and this has limitations given the limited manner in which the therapist can explain to the patient how to chew and the chewing motion becomes laborious and the patient loses interest quickly. This is especially true for a young child who did not naturally develop the ability to chew, as can occur with certain conditions such as cerebral palsy. A mouth piece that is designed specifically for the patient for the most comfortable fit will help reduce the laborious aspect of the training. In addition to the fit, the mouth piece may also have a number of sensors in the mouth piece that detect pressure, the location of the pressure and the motion of the mouth during the pressure. The sensors inside the mouth piece may have wireless transmitters that transmit the all of the data out to a central receiver that is connected to a control box.

In addition, as previously explained, current physical therapy is done with therapist stretching or moving a body part and then teaching a patient the motion. Patients will mirror (or attempt to mirror) to motion as instructed by the therapist. Feedback to the therapist is either through visual or manual monitoring by the therapist or by verbal feedback from the patient. A brace that is designed to fit the individual precisely and allow for free movement, support the movement or induce specified motion will allow constant and consistent therapeutic training. Using the feedback sensors, this device will monitor in real time and continuously record the history of movement, pressure, strain and stretch and provide necessary adjustments for enhanced therapeutic healing.

Data from the device may be communicated to a control box or other computing device. Biophysical data collected by the sensors may be transferred by secure wireless protocols to the control box before transfer to a database. The control box may also have access to the web and do a data mining search for specific new data on oro-motor or other training results. These results may be brought in and an algorithm may be used to compare and process against the chew or other motion data obtained. These results will be given to therapists that can then provide new motion routines. The routines may be intensive, lengthy and laborious. It is the repetitive process that teaches the more natural motion of chewing or the movement of a knee or ankle.

To accommodate the laborious aspects of intensive and lengthy, an algorithm may be used that takes measured pressure data from the mouth piece during motion and uses it in a video game like format. The game can be anything that needs input from the user and may be governed by rules modified by the healthcare provider. For example, a therapist can modify the goals/boundary conditions in a game (such as may be monitored via secure networks connected to the database) a a patient's performance improves. Most video games use pressure from hands and fingers to manipulate a character. Moving a joy stick left or right or pressure a button harder, all of these changes impose a response on a character or object in a game. This game may use the pressure, location, motion and speed to move the character or object in a game. Each game that may be an exercise of repetitive motion for training. The patient may then work toward a goal of perfection in the game which is what all videos games require.

As this progresses, the mouth piece may also be filled with motion inducers as well. These come in the form of piezoelectric, transducer, motors or any electrical and mechanical convertor. The mouth piece may teach the patient the motion by moving the chew piece in the specific spot or direction for the patient until the patient understands. This can also be coupled into a game like format. Additionally, this does not need to be a game-like format, but may still have visual feedback for the patient and the therapist. The electrically and mechanically functional mouth piece is wireless but it is under computer control.

The braces for any body part may also be filled with motion inducers as well. These come in the form of piezoelectric, transducer, motor or any electrical and mechanical convertor. The brace may aid in stretching, holding or moving in directions that enable healing. This can also be coupled into a game-like format. Additionally, this does not need to be a game-like format, but may still have visual feedback for the patient and the therapist. The electrically and mechanically functional device is wireless but it is under computer control.

In addition to braces, with rigid mechanical or firm structure, the personalized device may be a wrap or a bandage. Medical bandages exist, but these devices would have feedback sensors as well as electrical or mechanical input that would allow medication or an electrical impulse or a mechanical motion to come from the bandage. The bandage or wrap would be wireless and connected to a hand held device or computer for access to the data base. The bandage wrap may be set up to release medication at specified times as controlled by the computer.

All of the devices may have a data base collection protocol that shows motion, movement or action versus time. Any actuation or medication release done by the device may also be recorded, along with the magnitude, time, as well as any quantitative information.

In addition, the devices may be used during a therapy session to provide a health care provider real-time feedback. Thus the devices may be used to provide companion therapeutic/diagnostic capabilities.

According to one aspect, a personalized device for therapeutic training includes a therapeutic device body and electronic circuitry integrated into the therapeutic device body wherein the electronic circuitry comprises at least one sensor. The therapeutic device body is personalized for use by a patient through sizing and shaping the therapeutic device based on measurements of the patient and 3D printing at least a portion of the therapeutic device body and at least a portion of the electronic circuitry to make the personalized device both electrically and mechanically functional. The personalized device may be an oro-motor mouth piece, a brace, bandage, adhesive bandage, or a wrap. The wrap may include medication printed onto it. The personalized device may provide for dispensing medication. The personalized device of may include at least one motion inducer operatively connected to the electronic circuitry. The personalized device may be further configured to dispense medication. The electronic circuitry may include a transceiver for transmitting data from the at least one sensor or a transponder for communicating data from the at least one sensor. The electronic circuitry may be configured to encrypt data from the at least one sensor before communicating the data to a remote location.

According to another aspect, a method for performing therapy includes manufacturing a personalized device for therapeutic training, the personalized device for therapeutic training comprising (a) a therapeutic device body, (b) electronic circuitry integrated into the therapeutic device body wherein the electronic circuitry comprises at least one sensor, (c) wherein the therapeutic device body is personalized for use by a patient through sizing and shaping the therapeutic device based on measurements of the patient and 3D printing at least a portion of the therapeutic device body and at least a portion of the electronic circuitry. The method may further include acquiring data from the at least one sensor of the personalized device for therapeutic training. The method may further include obtaining additional data from a database of patient data. The method may further include sending the data from at least one sensor of the personalized device to a data base. The method may further include removing personally identifiable information from the data prior to sending the data to the data base. The method may further include using the data from the at least one sensor as input into a video game. The method may further include displaying the data on a display. The method may further include determining if a threshold is met based on the data and generating an alert if the threshold. The method may further include analyzing the data from the at least one sensor and additional data from one or more other patients using a data mining process.

According to another aspect, a method of tracking and comparing therapeutic training for chewing, or bending, or twisting, flexion or extension, adduction or abduction, or rotation using an intelligent personalized sensor system includes obtaining at least one of (a) data mined results from oro-motor training, (b) data mined results from physical therapy results, and (c) data mined results from real-time medication release. The step of obtaining is performed using at least one of (a) personalized 3D printed electrically and mechanically functional oro-motor mouth piece, (b) personalized 3D printed electrically and mechanically functional brace for any body part, and (c) personalized 3D printed electrically and mechanically functional wrap for any body part. The method further includes providing visual feedback and instruction in the form or a game or visual display that provides quantitative information.

DETAILED DESCRIPTION OF THE PREFERRED EMBODIMENTS

The present invention recognizes the need for remotely detecting motion inside the mouth piece of a training chewing device or a brace or a bandage or a wrap and utilizing that data to improve the quality and speed of treatment through the immediate closed-loop feedback to the patient based on preset goals or closed-loop through a networked database for comparison to population-scale anatomic biophysical data.

Figure 1:
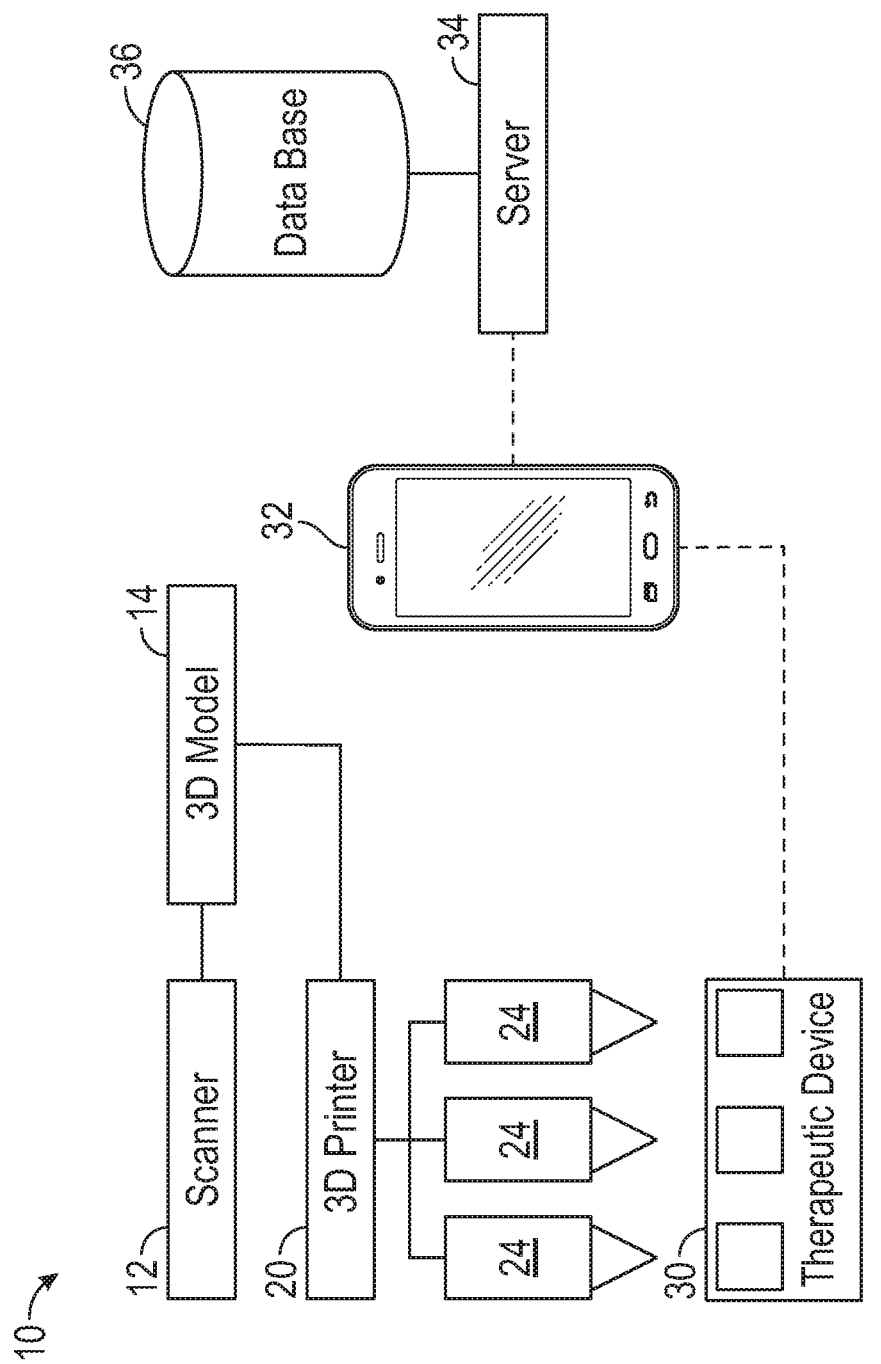
FIG. 1 is a block diagram on one example of a system.

FIG. 1 illustrates an overview of a system and methodology. As shown in the system 10, a scanner or other imaging device 12 may be used to image a patient and generate a 3D model 14 of a health monitoring device such as a training chewing device, a brace, or a bandage or wrap. The scanner or other imaging device 12 may be a computed tomography (CT) scanner, a camera, an ultrasound imaging device, or other type of scanner or imaging device. Photogrammetry methods may be used in order to assign specific dimensions to that which is imaged. Based on the imagery, measurements, or other available data, a three-dimensional model of a physical therapy device may be constructed. The physical therapy device can take a number of different forms including a mouth piece, a brace, a bandage, or a wrap. The 3D model 14 of the physical therapy device to be constructed is customized or personalized the physical parameters of the person for whom it is being constructed. The physical therapy device includes electronic components. The 3D model 14 may therefore also include electronic components such as sensors, transceivers, antennas, and other electronic circuitry.

Once the model is constructed, the physical therapy device may be manufactured using rapid manufacturing techniques and processes including by 3D printing with a 3D printer 20. The 3D printer 20 is preferably configured to print multiple materials from multiple nozzles 24. The 3D printer 20 allows for printing electronic circuitry including passive components, active components, conductive traces, insulators, as well as other materials. Thus, the physical therapy device may be constructed including electrical components and circuitry. If certain electronic components are required which cannot be printed with the 3D printer 20, then such components may be otherwise placed.

The resulting physical therapy device 30 is thus either personalized to an individual or utilized from a presized selection of choices based on the size/age of the patient. This personalization may include size of the device, shape of the device to fit the individual, as well as the positioning of sensors, size of the sensors, or other physical parameters of the physical therapy device. Note that where the device is manufactured in advance to a set of criteria, the device may still be manufactured in the same manner.

Data from the use of the device 30 may be recorded such as in a mobile device 32 or other computing device. This data may be communicated over a network to a server 34 and stored in a data base 36 or other computer readable storage medium. It should be understood that the availability of this data may be extremely useful in improving the efficacy of therapy in order to limit the time and effort of the patient and/or therapist while maximizing the beneficial results. In addition, the data base may be mined for any number of different purposes. Any number of different data mining algorithms may be used, including C4.5, k-means, support vector machines, Apriori, EM, PageRank, AdaBoost, 8. kNN, Naive Bayes, CART, or other which use decisions trees, cluster analysis, or other methodologies. Thus, data mining may be used to help provide therapeutic enhancements. The data base 36 will grow as the number of users grow and the available data sets grow. A central location of all the data is not be necessary when searching, however data may be stored at a central location if desirable. Various data privacy or data protection safeguards may be put in place. For example, in order to protect against disclosure of personal information, a patient's name may be separated from the data before sending this out to a world wide data base. Of course other types of anonymization or aggregation techniques may be used. In addition, all personal data from the sensor to the wireless device and the wireless device to a main computer may be encrypted to further provide privacy.

Figure 2:
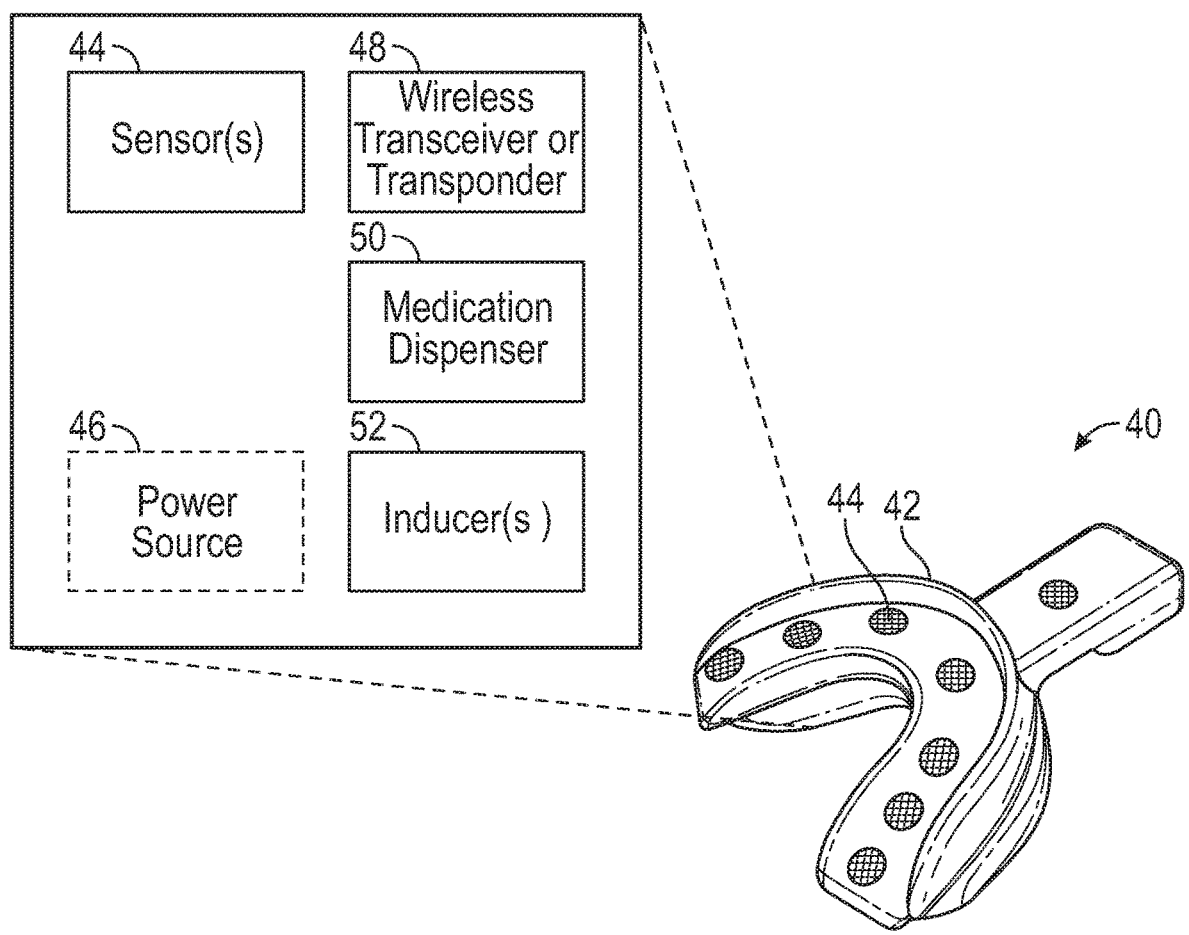
FIG. 2 is a diagram of one example of a mouth piece.

FIG. 2 illustrates one example of an oro-motor device in the form of a mouth piece 40. The mouth piece 40 is sized and shaped according to an individual's unique dimensions. One or more sensors 44 or other electronic components may be positioned on the mouth piece at any number of locations including on an external surface, within the mouth piece or elsewhere. There are a wide range of sensors that sense temperature, humidity, pressure, strain, crack, shock, vibration, direction, acceleration. Many of these can be 3D printed using strategic placement of diverse materials with specific properties. In addition, one or more motion inducers 52 may also be present. The sensors 44 and/or motion inducers 52 that are not optimal to print, can be placed and printed to. This aids in shrinking the overall electronics in that device. The wireless transmitter, transceiver, or transponder 48 has options that include a powerless transponder approach or Bluetooth or Near Field Communication or other low power options. The wireless sensor does not need to transmit a long distance. This can wirelessly connect to any wireless smart device. The wireless smart device can then connect to a wireless internet connection or a cell tower. The required power requirements to operate the sensor are much smaller than that power on a cell phone. Thus a power source 46 such as a battery may be smaller although it is contemplated that in some embodiments sensor data may be provided in a passive manner. The power to transfer the data is also very small, much smaller than the cell phone. The personalized fit will come from a scan of the mouth area. This can be done using a CT scan. The CT scan is converted to a solid model and the chew toy can be designed to fit in the 3D model. The chew toy can be 3D printed and including the electronics using 3D printed electronics. The results is an object that fits a specific individual with very low powered wireless sensors. Also one or more medication dispensers 50 may be present to release medication such as under computer control according to a schedule or in response to sensed data. The medication dispenser may take the form of a medication pump or other known forms.

Figure 3:
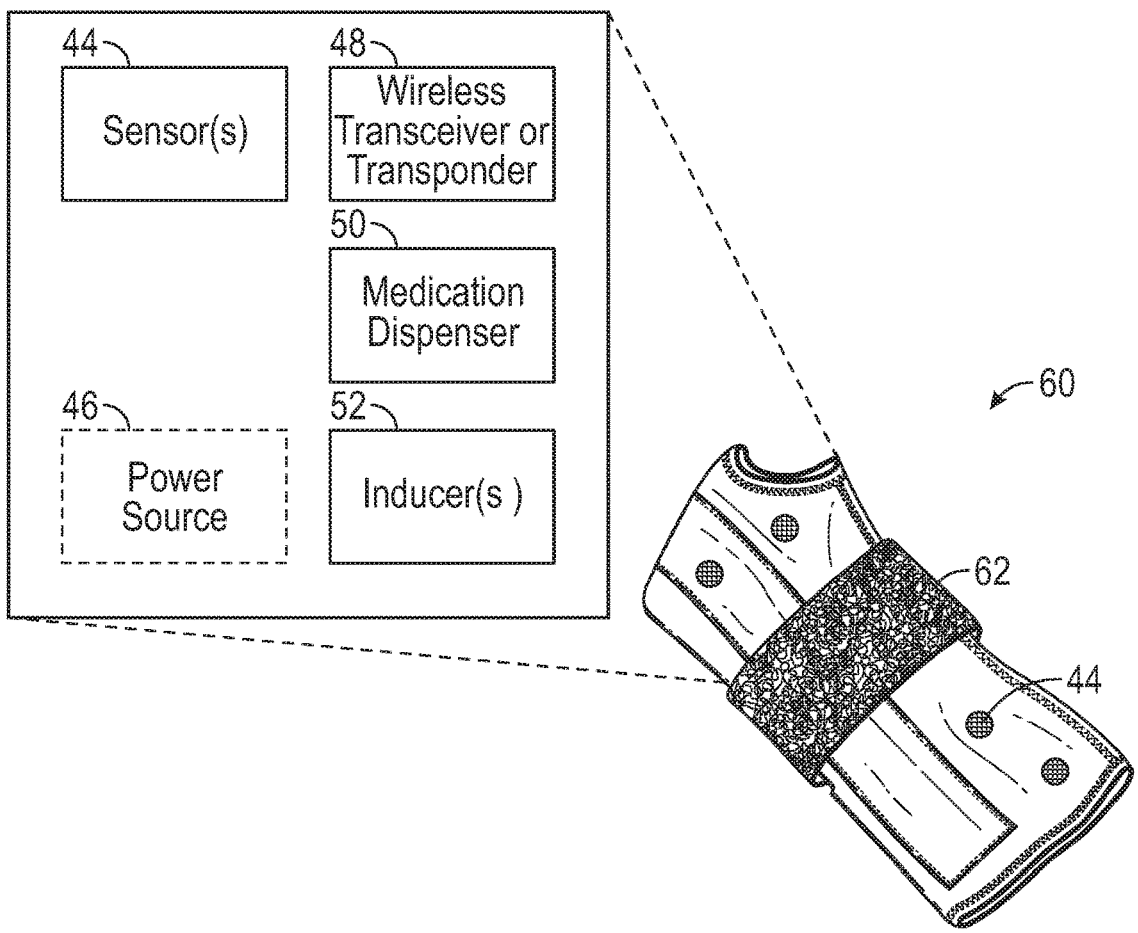
FIG. 3 is a diagram of one example of a brace.

FIG. 3 illustrates one example of a brace 60 with a body 62. The same approach can be used to make a brace for any part of the body that requires support. This includes, without limitation, wrist braces, elbow braces, back braces, knee braces, ankle braces, foot braces, head and neck braces, hip and thigh braces, shoulder braces and other types of braces. The area to fit can be scanned and for external braces there are a number of optical and laser scanners that can be used to obtain a 3D image. The 3D image may be a solid model and a brace can be made to fit that solid model. The brace and the necessary electronics and sensors in the brace can be 3D printed. FIG. 3 illustrates a wrist base having a plurality of sensors 44. Like the mouthpiece, the brace can include a wireless transmitter or transponder 48 and may include a power source 46 onboard unless a powerless transponder is used. In addition, one or more inducers 52 and one or more medication dispensers 50 may be present.

Figure 4:
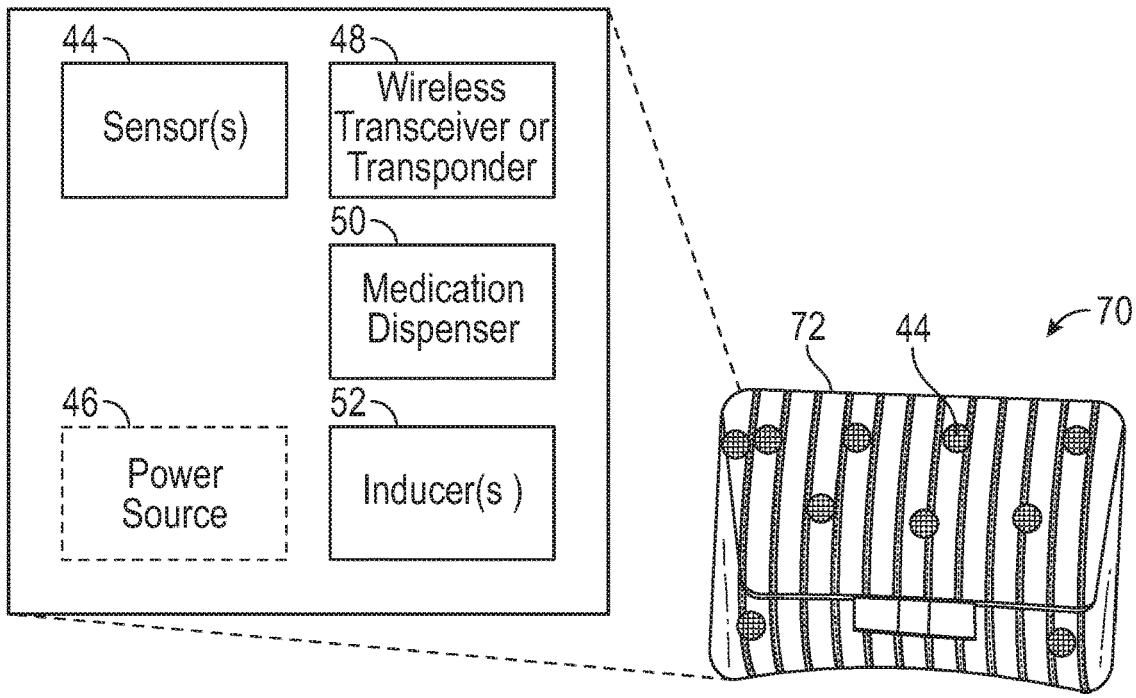
FIG. 4 is a diagram of one example of a wrap.

FIG. 4 illustrates one example of a wrap 70 having a body 72. The same approach as the chew toy and the brace can be taken for the wrap. There are a wide range of materials that can be printed that present different physical properties such as hardness, elasticity and other physical properties. In addition to the physical properties, there are diverse electrical and optical properties which allow the designers to accommodate a range of motions and support. There may be motion inducers present. In addition, there may be medications which are present on the wrap such that the medications are absorbed via contact with the skin. Where medication is present, the medication may be added through 3D printing as well with the dosage determined in a manner consistent with desired treatment for the patient.

In addition to sensors, the various physical therapy devices may include motion devices or inducers 52 to provide forced motion. Using motion devices such as elastic properties of a material, piezo, motors or any electrically induced mechanical motion, small motions can aid in guiding the patient how to move properly for training. For larger motions or more force, larger device can be made. This may be programmed to obtain a specific profile of movement for therapy. This may be performed at a physical therapists office with trained therapists now, this would mimic those motions. In addition to these motions, there is also the chew motion that can be replicated to allow the patient to practice under guidance.

Figure 5:
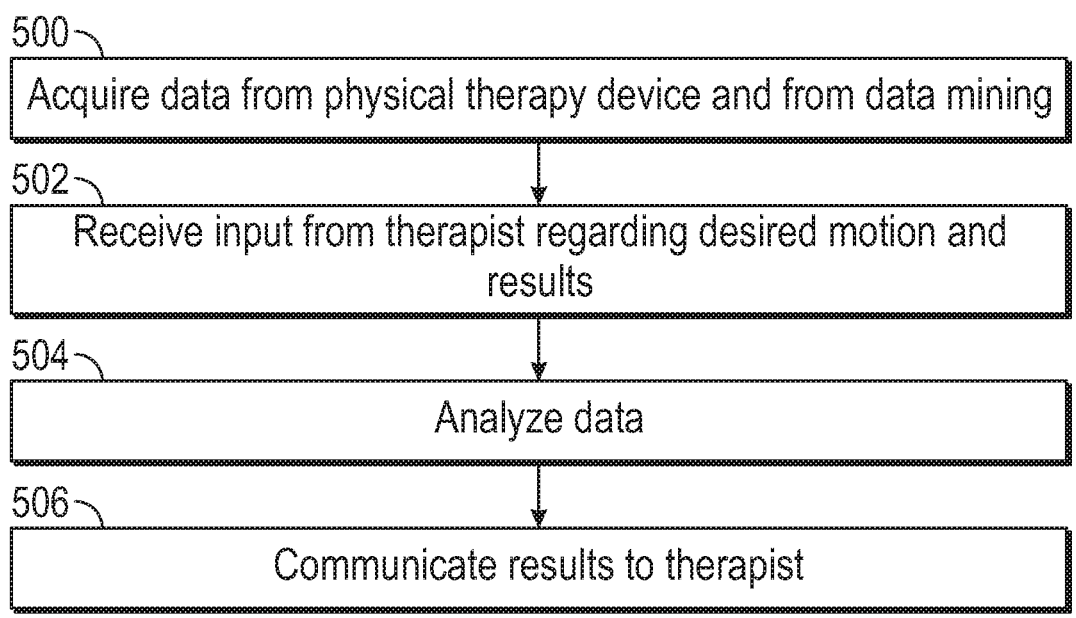
FIG. 5 is a diagram of one example of a method.

FIG. 5 illustrates one example of an algorithm which may be used. In step 500 data is acquired from the mouth piece, brace, wrap, or other physical device. In addition, data may be taken from data mining. In step 502, the therapist may input desired motion and results. In step 504 the data may be analyzed such as by an algorithm that will contrast and compare and then filter out unrelated data and then, using a time frame, combine the two sets of data to see if a trend can be established and present that back to the therapist in step 406. The information conveyed back to the therapist may contain pre and post therapeutic work and the results for each therapy.

Information can be provided to physical therapists or other health care providers in any number of forms, including while a patient is using a physical therapy device in order to assist with evaluation of a patient. This evaluation may be real time, provide a virtual prediction or show past results in a visual plot versus time or pressure versus motion or pressure versus location to enhance and optimize the output. Visual feedback may be used to enhance the overall evaluation of the process. Charts, graphs and other visual effects provide a clear picture of what has been done. The visual reference may be the path that each mechanical device will take thus allowing the therapists to get a clear understanding of what they are trying to accomplish. This could also be used to predict future or optimized therapies.

Figure 6:
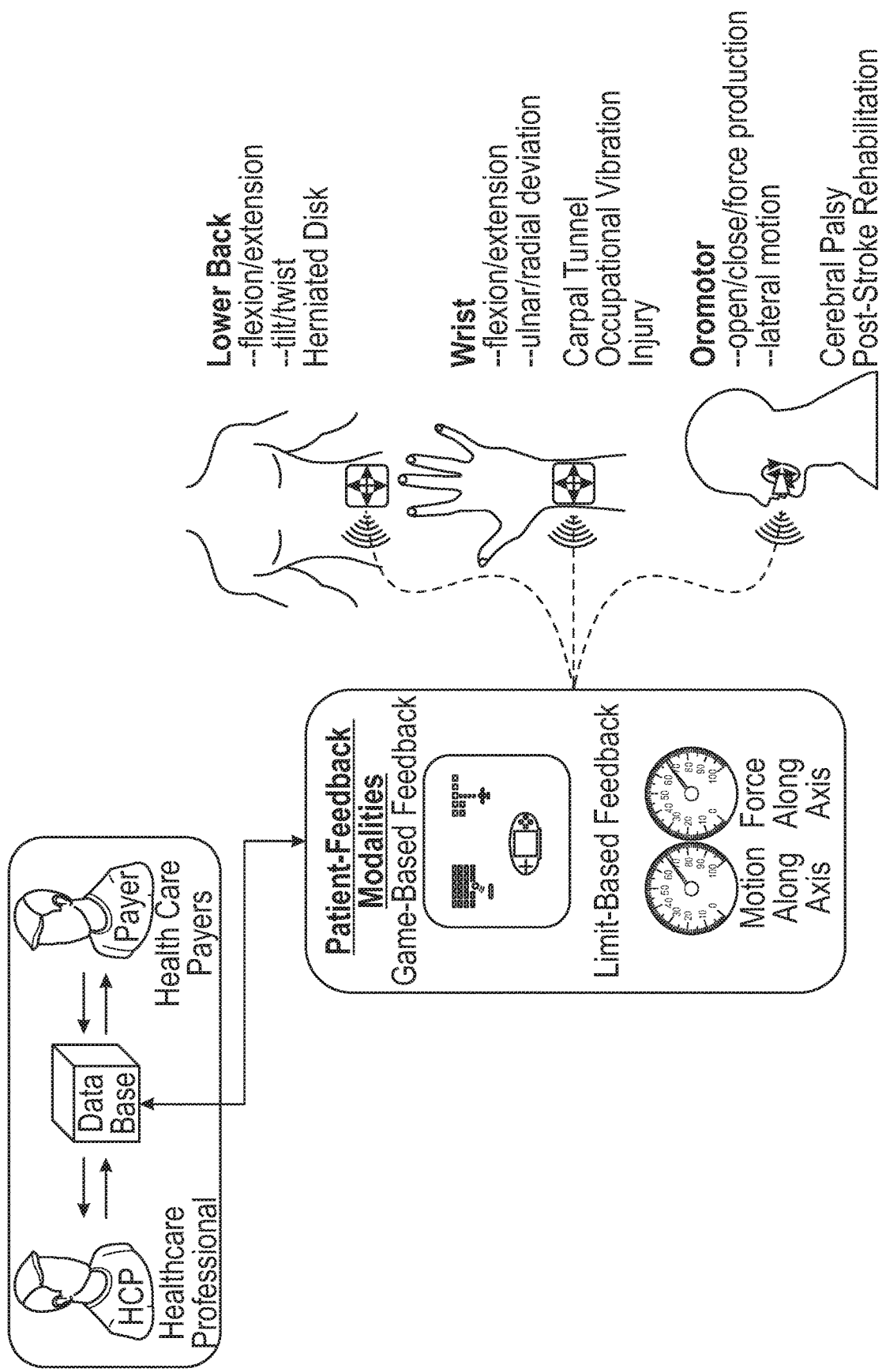
FIG. 6 is another diagram illustrating patient-feedback modalities.

FIG. 6 illustrates an overview of how the data acquired using the sensors may be used to provide feedback. As shown in FIG. 6, patient-feedback modalities include game-based feedback and limit-based feedback.

For game-based feedback, in order to provide motivation and encouragement to do the therapy required, the motion can be turned into a control device for a game in a similar way a joystick controls a character, the desired motion can be the input and this will encourage the patient to perform the routine, but also aid in longer periods of sustainment. Thus, patient compliance with physical therapy may be increased. It is noted that the game may be simple in nature or more complex. The activity required by the user to play the game should be consistent with the physical therapy required and it is contemplated that the game may receive as inputs information which may be used to adapt or configure the game to modes or settings most conducive to a user's therapy. This may include game speeds, game durations, game complexity, or other information.

Another type of feedback which may be provided to a user is limit-based feedback. Thresholds or limits may be associated with the motion of a patient. This may include limits associated with motion along a particular axis or force along a particular axis or other combinations of motions and/or force. Thus, a patient may be alerted when the thresholds or limits are exceeded to prevent the patient from hurting themselves. Other types of patient-feedback modalities may also be used.

FIG. 6 also illustrates examples of different types of motion which may be associated with physical therapy for certain conditions. For example, where a patient has a herniated disk motions such as flexion/extension and tilt/twist of the lower back may be performed. Where the patient has carpal tunnel or an occupational vibration injury motions such as flexion/extension and/or ulnar/radial deviation may be performed with the wrist. Where the patient has cerebral palsy or is undergoing post-stroke rehabilitation motions such as open/close/force production, and lateral motion may be performed. Of course, it is contemplated that any number of types of motion for any number of different parts of the body may be performed as a part of physical therapy.

In addition, data collected may be stored in a database. It is contemplated that the data may be used by any number of parties associated with health care of the individual provided appropriate privacy protections and permissions are in place. For example, this data may be shared with the physical therapist or other health care provider and may be associated with a payer such as an insurance company, employer, government entity, or other. One reason for sharing such information is to demonstrate that a patient has complied with a particular physical therapy regimen.

Figure 7:
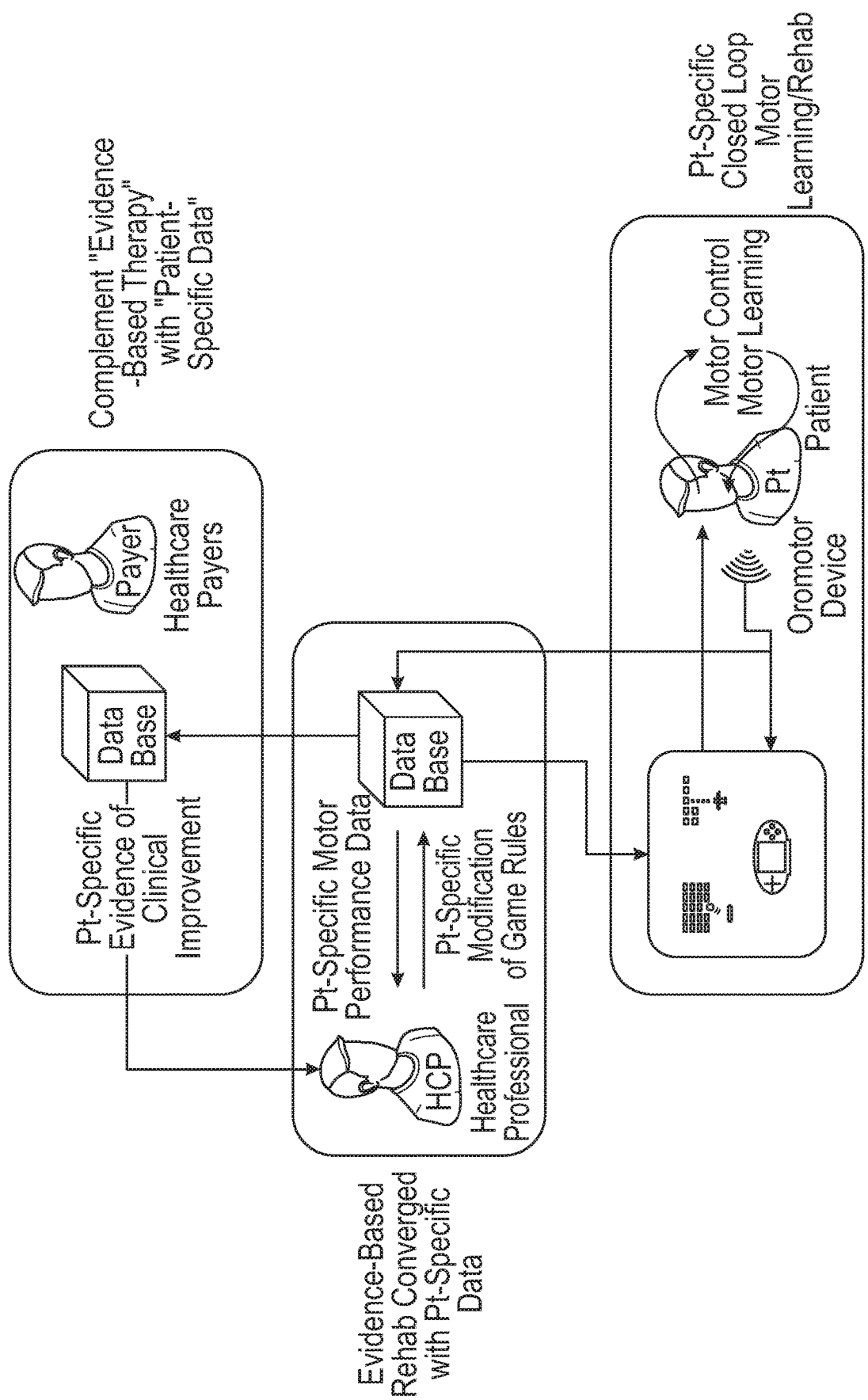
FIG. 7 is another diagram illustrating examples of data flow.

FIG. 7 further illustrates how data from a physical therapy device may be used by a patient as a part of physical therapy. In this instance the patient may use an oromotor device to assist with motor control and motor learning as a part of a rehabilitation. The patient may be using the oromotor device to control an aspect of a game. Information regarding the movement of the patient may be communicated to a data base which a health care professional has access to. The health care professional may receive patient specific motor performance data and may provide physical therapy specific modifications of game rules or parameters. Thus, the health care professional can provide evidence-based rehabilitation converged with patient specific data. Information from the data base may also be received into a database from a health care payer who will be able to complement evidence-based therapy with patient specific data for any number of reasons including to document patient specific evidence of clinical improvement or to provide evidence-based reimbursement of physical therapy.

What is claimed is:

1. A system comprising:
   (a) a personalized device for therapeutic training, comprising:
   a therapeutic device body;
   electronic circuitry integrated into the therapeutic device body wherein the electronic circuitry comprises at least one sensor;
   (b) a three dimensional model of the personalized device for therapeutic training using measurements of a patient, wherein the three dimensional model models both the therapeutic device body and the electronic circuitry integrated into the therapeutic device body and defines size of the personalized device for therapeutic training so as to fit the patient, shape of the personalized device for therapeutic training so as to fit the patient, positioning of the at least one sensor within the personalized device for therapeutic training so as to fit the patient, and size of the at least one sensor within the personalized device for therapeutic training so as to fit the patient;
   wherein the therapeutic device body is constructed according to the three dimensional model, wherein at least a portion of the therapeutic device body and at least a portion of the electronic circuitry are 3D printed to make the personalized device for therapeutic training both electrically and mechanically functional;
   wherein the personalized device for therapeutic training is in operative communication with a video game such that data from the at least one sensor is communicated to the video game as input as a part of the therapeutic training.

2. The system of claim 1 wherein the personalized device is an oro-motor device.

3. The system of claim 1 wherein the personalized device is a brace.

4. The system of claim 1 wherein the personalized device is selected from a set consisting of a wrap, a bandage, and an adhesive skin applique.

5. The system of claim 1 wherein medication is printed onto the personalized device.

6. The system of claim 1 further comprises at least one motion inducer operatively connected to the electronic circuitry.

7. The system of claim 1 wherein the personalized device is further configured to dispense medication.

8. The system of claim 1 wherein the electronic circuitry further comprises a transceiver for transmitting data from the at least one sensor.

9. The system of claim 1 wherein the electronic circuitry further comprises a transponder for communicating data from the at least one sensor.

10. The system of claim 1 wherein the electronic circuitry is configured to encrypt data from the at least one sensor before communicating the data to a remote location.

11. The system of claim 1 wherein the electronic circuitry further provides for providing feedback to the patient.

12. A method for performing therapy comprising:
   acquiring measurements of a patient for sizing and shaping a personalized device for therapeutic training;
   constructing a three dimensional model of the personalized device for therapeutic training using the measurements, wherein the three dimensional model defines size of the personalized device for therapeutic training so as to fit the patient, shape of the personalized device for therapeutic training so as to fit the patient, positioning of sensors within the personalized device for therapeutic training so as to fit the patient, and size of the sensors within the personalized device for therapeutic training so as to fit the patient;
   manufacturing the personalized device for therapeutic training, the personalized device for therapeutic training comprising (a) a therapeutic device body, (b) electronic circuitry integrated into the therapeutic device body wherein the electronic circuitry comprises the sensors, (c) wherein the therapeutic device body is personalized for use by the patient through sizing and shaping the therapeutic device body based on the measurements of the patient and 3D printing at least a portion of the therapeutic device body and at least a portion of the electronic circuitry according to the three dimensional model;
   acquiring data from the sensors of the personalized device for therapeutic training; and
   using the data from the sensors as input into a video game.

13. The method of claim 12 further comprising obtaining additional data from a database of patient data.

14. The method of claim 12 further comprising sending the data from the sensors of the personalized device to a data base.

15. The method of claim 14 further comprising removing personally identifiable information from the data prior to sending the data to the data base.

16. The method of claim 12 further comprising displaying the data on a display.

17. The method of claim 12 further comprising determining if a threshold is met based on the data and generating an alert if the threshold is met.

18. The method of claim 12 further comprising analyzing the data from the sensors and additional data from one or more other patients using a data mining process.

19. A method of tracking and comparing therapeutic training for chewing, or bending, or twisting using an intelligent personalized sensor system comprising:
   obtaining at least one of (a) data mined results from oro-motor training, (b) data mined results from physical therapy results, and (c) data mined results from real-time medication release;

wherein the obtaining is performed using a personalized 3D printed electrically and mechanically functional oro-motor mouth piece; and providing visual feedback and instruction in a form of a game that provides quantitative information.

20. A method for performing therapy comprising:

acquiring measurements of a patient for sizing and shaping a personalized device for therapeutic training;

manufacturing the personalized device for therapeutic training, the personalized device for therapeutic training comprising (a) a therapeutic device body, (b) electronic circuitry integrated into the therapeutic device body wherein the electronic circuitry comprises at least one sensor, (c) wherein the therapeutic device body is personalized for use by the patient through sizing and shaping the therapeutic device body based on the measurements of the patient and 3D printing at least a portion of the therapeutic device body and at least a portion of the electronic circuitry;

acquiring data from the at least one sensor of the personalized device for therapeutic training; and using the data from the at least one sensor as input into a video game.

\* \* \* \* \*